United States Patent [19]

Vallana

[11] Patent Number: 4,892,540
[45] Date of Patent: Jan. 9, 1990

[54] TWO-LEAFLET PROSTHETIC HEART VALVE

[75] Inventor: Franco Vallana, Turin, Italy
[73] Assignee: Sorin Biomedica S.p.A., Saluggia, Italy
[21] Appl. No.: 183,774
[22] Filed: Apr. 20, 1988
[51] Int. Cl.⁴ ............................................. A61F 2/24
[52] U.S. Cl. ..................................... 623/2; 137/512.1; 137/527
[58] Field of Search ............................. 623/2; 137/527

[56] References Cited

U.S. PATENT DOCUMENTS 4,363,142 12/1982 Meyer .
4,601,719 6/1986 Totten .

FOREIGN PATENT DOCUMENTS 0050439 4/1982 European Pat. Off. ................. 623/2
0091746 3/1983 European Pat. Off. .
86/05383 9/1986 PCT Int'l Appl. ...................... 623/2
1304810 4/1987 U.S.S.R. ................................. 623/2
2074699 11/1981 United Kingdom ................... 623/2

Primary Examiner—Richard J. Apley
Assistant Examiner—Stephanie L. Iantorno
Attorney, Agent, or Firm—Hedman, Gibson, Costigan & Hoare

[57] ABSTRACT

A prosthetic heart valve (valve) composed of a base ring adapted to house a suture ring in its exterior and two leaflets arranged to assume an open position and a closed position in order to regulate the blood flow in one direction, wherein the base ring is provided with two recesses with curved surfaces situated in diametrically opposite positions. Each of the recesses communicate with the exterior through a chimney-like aperture formed in the body of the base ring in correspondence with the recess. Each of the curved recesses has a substantially flat surface bounding its upper part and two spherical bottom surfaces in its lower part, separated by a separator body essentially in the shape of a semispherical-nail.

8 Claims, 4 Drawing Sheets

TWO-LEAFLET PROSTHETIC HEART VALVE

The present invention relates to valve prostheses or, in short, to heart valves which are fitted as replacements for natural valves should the latter be malformed. The invention concerns, in particular, heart valves of the type comprising two leaflets which are arranged to open when a pressure difference is established in a certain direction and to close again the moment the pressure difference is reversed.

These prosthetic valves are generally constituted by a base ring of rigid material which houses a ring of material which can be sutured to the heart tissue in its generally recessed outer surface. A structure with one or more leaflets linked in some way to the base ring and arranged to oscillate from a position in which the passage created in the base ring is open and a position in which it is closed regulates the blood flow in one-direction.

The characteristics of such prosthetic heart valves vary with the form of the leaflets and of the base ring and with the criteria of operation of the assembly; these criteria determine the means provided for causing the oscillation of the leaflets, means which generally involve both the bodies of the leaflets and that of the base ring.

There are various requirements, both mechanical and biological, which a prosthetic heart valve must satisfy.

Of these requirements the following may be considered fundamental:

speed of response and speed of closure of the leaflets to avoid backflow;

absence of highly curved surfaces, both in the leaflets and in the base ring, to avoid turbulence and haemolysis of the blood as well stagnation thereof; and structural profiles which do not project too far axially to avoid harmful contact with the walls of the heart.

Other requirements concern the materials used in the prosthetic valve, and amongst these the criterion of compatibility of the materials with the biological masses, and in particular with the blood, holds first place.

The evolution of heart valve models with time has satisfied the aforesaid requirements by successive approximations. Changes have been made from ball valves to disc valves, to cuspidate leaves; more recently, there has been a proposal of valves with two leaflets hinged in some way to the base ring with their opening and closing travel arrested in some way.

In spite of continual progress, there are still many problems which have not been resolved satisfactorily. that is, there are still difficult points, essentially two in number: the way in which the leaflets are pivoted in the base ring and the structures for stopping the opening and closing of the leaflets.

In some models the leaflets pivot about pins fixed to the base ring; in other models the pins are carried by the leaflets and held in suitable cavities formed in the base ring.

These pin solutions, however, have revealed quite serious deficiencies due to the stagnation of blood in the cavities and to the relatively complex structure of the hinge region.

The arrest of the closing and opening of the leaflets is generally achieved by structures with steps, corners or projecting edges: these parts have also been found unsatisfactory as sites which are prone to turbulence and haemolysis.

The prosthetic heart valve which is the subject of the present invention prevents these and other problems, has an extremely simple and compact structure reduced to the essential elements without the addition of projecting parts, and is safe, prompt and quick in operation.

The present invention has the further advantage that it does not give rise to regions where the blood may stagnate and that it does not have possible haemolysis and turbulence points.

A further characteristic of the heart valve of the present invention is that it is absolutely biocompatible, since the materials are covered with a thin, dense, homogeneous film of carbon in the turbostratic state which is that state which has the greatest degree of biocompatibility.

The main subject of the present invention is a prosthetic heart valve composed of a base ring adapted to house a suture ring in its exterior and two leaflets which can assume an open position and a closed position in order to regulate the blood flow in one direction, in which the base ring is provided with two recesses with curved surfaces situated in diametrally opposite positions; each of the recesses communicating with the exterior through a chimney-like opening formed in the body of the base ring in correspondence with the recess, each of the curved recesses having a pseudo-flat surface bounding its upper part and two spherical bottom surfaces in its lower part, separated by a separator body of semi-spherical-nail shape.

These and other characteristics of the present invention will become clearer from the following description of a preferred embodiment thereof taken in combination with the appended drawings, in which.

Figure 1:
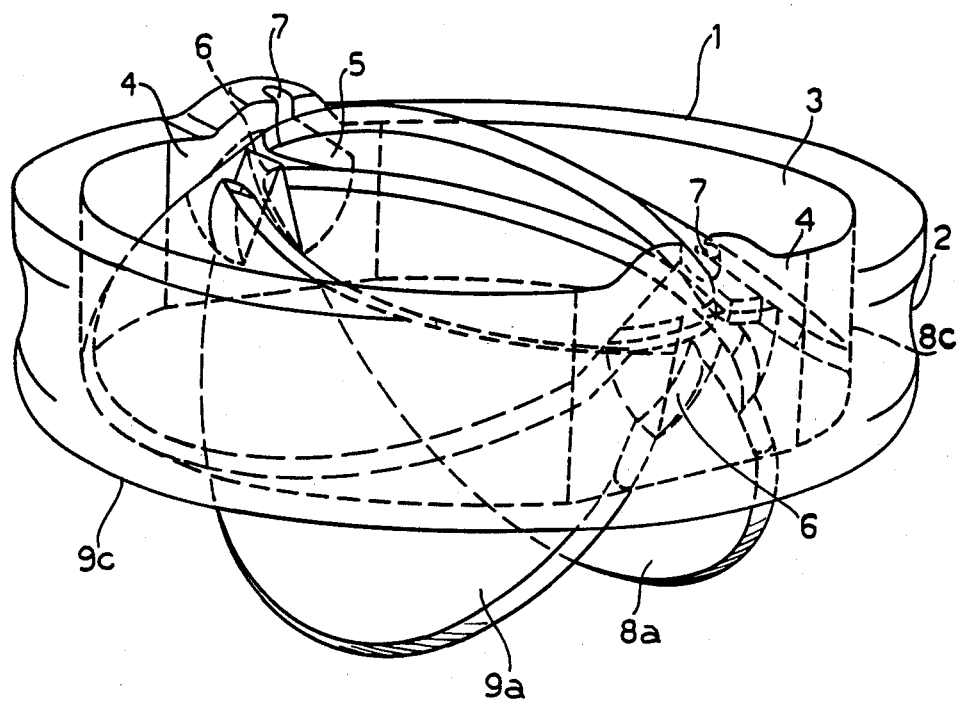
FIG. 1 is a perspective view of the prosthetic valve unit of the present invention with the leaflets both in the open and in the closed positions.

The body of the heart valve which will now be described has elements which are identical and elements which are mirror imaged. For simplicity of description, these elements have been labelled with the same reference numerals. Different numerals, however, have been provided where any ambiguity could arise.

With reference to FIG. 1, a substantially cylindrical base ring, indicated 1, has a recess 2 in its outer surface which can house a suture ring (not shown in the drawing) of relatively soft material, generally of textile fibre, which can be sutured to the heart tissue.

The inner surface 3 of the ring 1 is cylindrical except for two diametrally-opposite portions in which the cylindrical surface is replaced by two parallel flat surfaces 4 which cause corresponding thickenings of the body of the ring 1. Within each of these thicker parts is a recess 5 with curved surfaces divided into two mirror-imaged sectors by a separator body 6 whose function will be seen below.

Each recess 5 extends upwardly into a chimney-like aperture 7 which puts the recess into communication with the exterior.

Two leaflets, indicated 8 and 9, are shown both in the open position (8a, 9a) and in the closed position (8c, 9c) of the valve.

Figure 2:
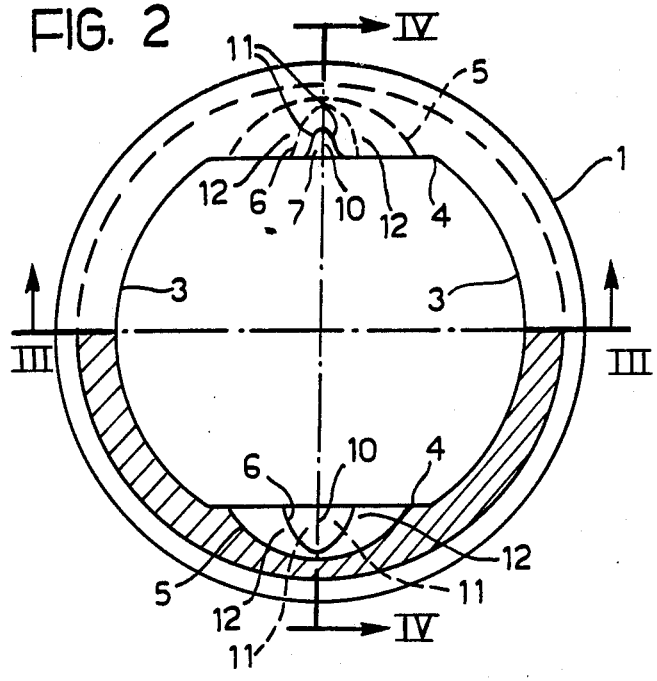
FIG. 2 is a partially-sectioned schematic plan view of the base ring of the valve indicated 1 in FIG. 1.

With reference to FIG. 2, in this the base ring 1 of the valve is shown in plan in two different ways: above the line III—III is a view from above, below the line is a section of the ring in a horizontal plane passing through the top of the separator bodies 6 (FIG. 1).

The inner aperture of the base ring 1 (FIG. 2) is constituted by two circumferential arcs 3 connected by two chords 4; the curved recesses 5 are, to a first approximation, spherical segments; in their central parts are the separator bodies 6.

Reference 10 indicates the line at which two faces 11 of the separator body 6 meet.

Reference 12 indicates the lines at which the faces 11 of the separator body meet the part-spherical bottom surfaces of the recesses 5.

Figure 3:
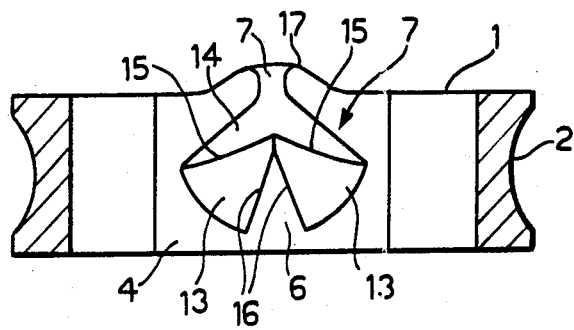
FIG. 3 is a diametral section of the base ring of the valve, taken on the line III—III of FIG. 2.
Figure 4:
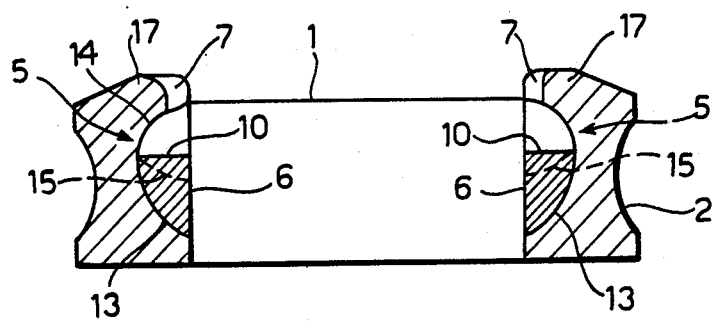
FIG. 4 is a diametral section of the base ring of the valve, taken on the line IV—IV of FIG. 2.

The said recess is seen from the front in FIG. 3 which shows the section taken on the line III—III of FIG. 2, and in vertical section in FIG. 4 which shows a section taken on the line IV—IV of FIG. 2. It is constituted by two lower spherical segment-shaped parts 13 (FIG. 3) separated by the separator body 6, and by a roof 14 (FIGS. 3 and 4) which constitutes a substantially flat surface. The lines at which the two segments meet are indicated 15.

It should be noted that, for simplicity and clarity of graphical representation, the meeting of the flat or curved surfaces is represented by lines in all the drawings illustrating the present invention; in reality, these are connection zones, since all the changes from one surface to another are rounded.

Each of the separator bodies 6 in the recesses 5 is essentially half a spherical nail whose curved sides are the meeting lines 12 (FIG. 2); the triangle-section which delimits the half-nail is the vertical face 4 (FIG. 2, 3); the corners are the line 10 (FIGS. 2, 4) and the line 16 (FIG. 3) which delimit the face on the flat surface 4.

The chimney-like aperture 7 is formed in correspondence with the curved recesses 5 centrally thereof (FIGS. 3, 4) and a slightly raised part 17 may be provided on the base ring 1 in correspondence therewith.

Figure 5:
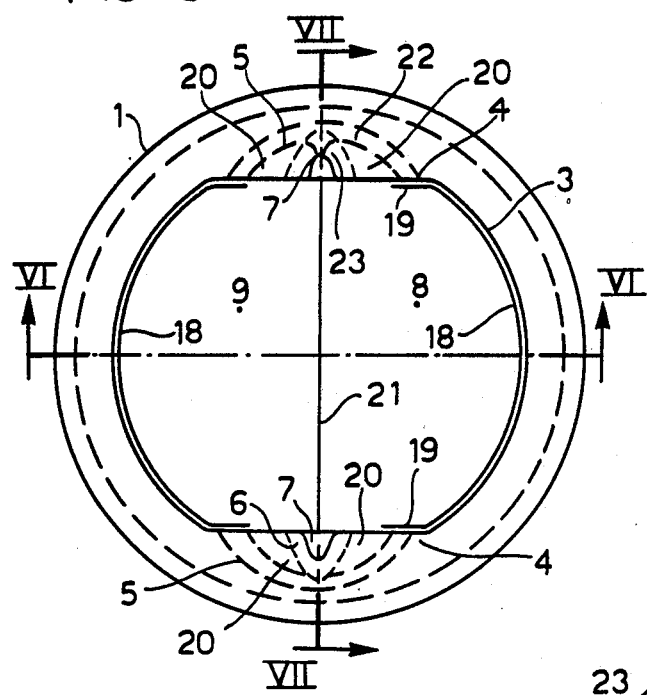
FIG. 5 is a plan view of the valve of FIG. 1 with the leaflets in the closed position.

With reference to FIG. 5, this shows the leaflets 8 and 9 in plan, in the closed position. Each of these is circumscribed by: an outer edge 18 which is essentially an elliptical arc which follows the inner surface of the base ring 1; two straight portions 19 which follow the flat surfaces 4 of the ring; the curved outlines of two tongues 20; and, finally, by the inner edge 21, which is essentially elliptical in shape.

Each leaflet has its own plane of symmetry, shown by the line VI—VI in FIG. 5.

The profile of each tongue 20 is divided into two curved parts, the first, indicated 22, is a circumferential arc with a radius of curvature which is less than or equal to the radius of curvature of the spherical bottom surface of the recess 5, the second, indicated 23, is a segment of an ellipse and is formed by an extension of the internal edge 21 of the leaflet.

Figure 6:
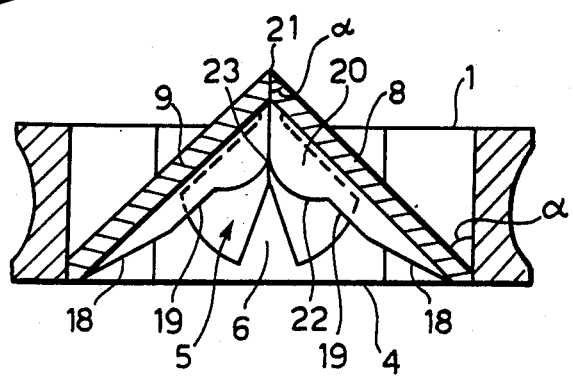
FIG. 6 is a diametral section of the valve with the leaflets in the closed position, taken on the line VI—VI of FIG. 5.

The leaflets 8 and 9 have straight profiles in the front-to-back direction, as can be seen from FIG. 6 which is a section in a plane perpendicular to the base ring 1, taken on the diameter VI—VI of FIG. 5. Each of these leaflets is essentially a curved surface generated by a straight line segment, supported at the inner edge 21 and at the outer edge 18 and displaced parallel to itself from the end of one tongue 20 to the end of the diametrally opposite tongue.

The edge 21 of each leaflet is a flat face at an angle alpha to the outer surface of the leaflet, this angle being equal to the angle between the surface of the leaflet itself and the generatrix of the internal cylindrical surface 3 of the ring, obviously with the leaflets in the closed position.

Figure 7:
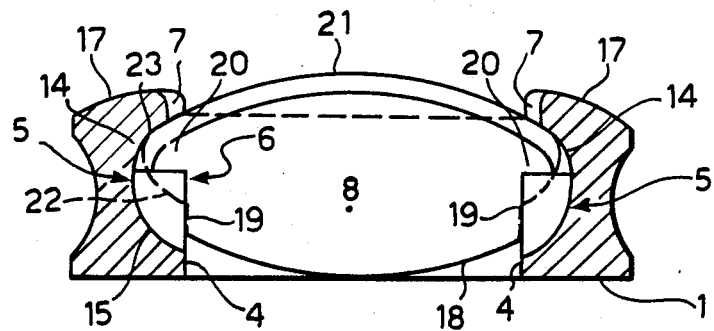
FIG. 7 is a diametral section of the valve with the leaflets in the closed position, taken on the line VII—VII of FIG. 5.

A section of the valve taken on the line VII—VII of FIG. 5 is shown in FIG. 7. From this, both the shape of the leaflet and its tongues 20, and the positioning of the tongues within the curved recesses 5, can be seen more clearly.

The closed position of the leaflets can be seen from a combination of the three FIGS. 5, 6 and 7. The inner edges 21 mate throughout their entire thicknesses along the diameter of the aperture of the base ring 1, that is, between the chimney-like apertures 7. The tongues 20 of each leaflet are inserted in the upper parts of the recesses 5, that is, in the parts which are delimited at the top by the roofs 14, without, however, touching their bottom surfaces. The straight portions 19 follow the flat surfaces 4 of the base ring 1 and the outer edges 18 of the leaflets bear against the inner surface 3 of the base ring 1.

Figure 8:
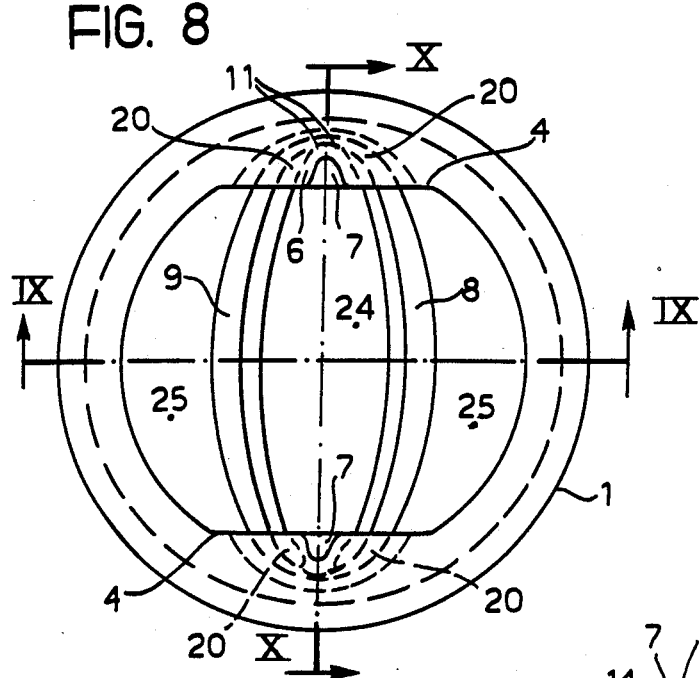
FIG. 8 is a plan view of the valve of FIG. 1, with the leaflets in the open position.
Figure 9:
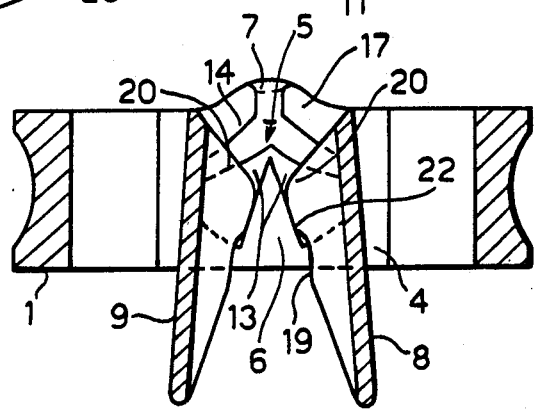
FIG. 9 is a diametral section of the valve with the leaflets in the open position, taken on the line IX—IX of FIG. 8.
Figure 10:
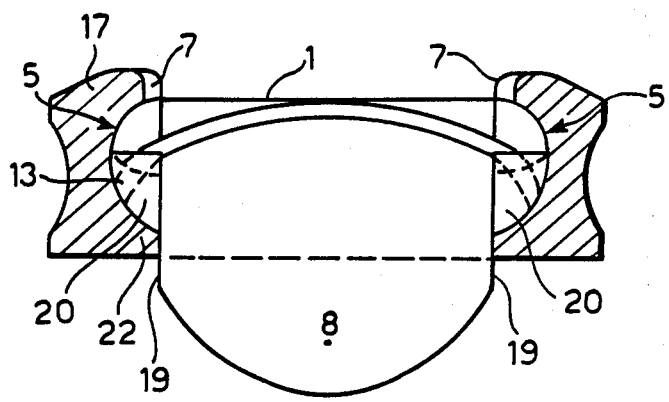
FIG. 10 is a diametral section of the valve with the leaflets in the open position, taken on the line X—X of FIG. 8.

The positions of the leaflets 8 and 9 when the valve is open can be seen in FIGS. 8, 9 and 10. In this case, the tongues 20 are inserted in the lower sectors 13 (FIGS. 9 and 10) of the corresponding curved recess 5. The circumferential arcuate parts 22 of the tongues 20 bear against the faces 11 (FIG. 8) of the separator body 6, whilst the point at which the straight portion 19 of the leaflet (FIGS. 9 and 10) and the curved part 22 of the tongue 20 meet bears on the connection between the bottom surface of the curved recess 5 and the flat surface 4 of the base ring 1.

The aperture of the base ring 1 is divided into three regions: a central region 24 (FIG. 8) between the open leaflets, and two lateral regions 25 between the outer surfaces of the leaflets and the base ring 1. The three parts are hydraulically equivalent so as not to cause differences between the flow of blood in the central region 24 and in the lateral regions 25. This equality of flow in the three regions is the best condition for reducing turbulence.

The kinematics of the valve in operation are as follows.

When, with the valve closed, that is, with the leaflets in the position shown in FIGS. 5, 6 and 7, there is a positive pressure difference in the direction of the arrow of FIG. 9; this presses on the upper surfaces of the leaflets 8 and 9 thrusting them downwards. There is thus both a simultaneous pivoting of the leaflets which brings them into the position of FIGS. 8, 9 and 10, and a translational movement of the leaflets themselves in the direction of the blood flow. More precisely, each tongue 20 (FIG. 6) slips down into the sector 13 of the recess 5 from its upper position in the recess in which it bears against the roof 14. The simultaneous pivoting and sliding of the leaflets 8, 9 obviously also cause pivoting of the tongues 20 which had been bearing against the faces 11 (FIG. 8) of the separator body 6.

The pivoting of the leaflets is arrested by the separator body 6 and the sliding of the leaflets in the direction of the flow is arrested by the abutment of the circumferential-arc portions 22 of the tongues 20 against the bases of the spherical sectors 13 of the recesses 5. In this position parts of the straight portions 19 of the leaflets lie against the flat surfaces 4 (FIG. 9) of the base ring 1.

When the pressure difference starts to reverse, the leaflets 8 and 9 are urged to pivot and to move upwardly and the operations seen for opening are repeated in reverse order for closing.

The closure is stopped by three actions:
the inner edges 21 of the leaflets mate with each other over their entire thicknesses; the outer edges 18 of the leaflets contact the inner wall 3 of the ring 1; the tongues 20 of the leaflets contact the roofs 14 of the curved recesses 5.

The two degrees of freedom in the movement of the leaflets which make the rotary-translatory movement possible also enables the recesses 5 to be washed. In fact, both during the phase in which the leaflets move from the closed position into the open position, and in the open phase, the blood flow also passes through the curved recesses 5 and through the chimney-like apertures 7, thus washing the insides of the recesses. This washing drastically reduces the danger of stagnation and the formation of clots or fibrous deposits.

The described embodiment of the present invention may be modified and varied without thereby departing from the scope of the invention.

I claim:

1. A prosthetic heart valve for reducing the formation of thrombi comprising:
   (a) a base ring adapted to house a suture ring in its exterior for suturing to the heart tissue, wherein said base ring includes an inner surface with walls forming two diametrically opposed recesses which communicate with the exterior, and wherein said recesses include:
      (i) an upper portion having a substantially flat surface with an opening therebetween;
      (ii) a lower portion separated into two spherical bottom surfaces by a separator body wherein said separator body extends from said lower portion of said recess and said separator body comprises a wedge shape to provide an opposing recess portion on each side of said separator body; and
   (b) two leaflets having an open position and a closed position for regulating the flow of blood in one direction wherein each of said leaflets has a pair of tongues with one tongue on each side of each leaflet positioned in a recess portion of each of said opposing recesses, and wherein said tongues of said leaflets have continuously changing point contact with the walls of said opposing recesses when said leaflets move between said open position and said closed position for preventing the formation of thrombi as the blood flows from and through said recesses.

2. A prosthetic heart valve according to claim 1, wherein each of said tongues of said leaflets is adapted for insertion in one of said recesses and move within said recesses in a double rotary-translatory action during the closing and opening of the valve.

3. A prosthetic heart valve according to claim 1, wherein said separator body acts as a travel-limit stop for the pivoting of said leaflets during the opening of the valve.

4. A prosthetic heart valve according to claim 1, wherein each of said spherical bottom surfaces of said recesses acts as a travel-limit stops for the translational movement of said leaflets during the opening of the valve.

5. A prosthetic heart valve according to claim 1, wherein, said leaflets divide the internal aperture of the base ring into three hydraulically equivalent parts, resulting in three blood flows of substantially the same capacity when said leaflets are in said open position.

6. A prosthetic heart valve according to claim 1, wherein the section of each of said leaflets in its own plane of symmetry is a straight line segment.

7. The prosthetic heart valve of claim 1, wherein each of said leaflets have an elliptically-arcuate outer edge and an elliptically-arcuate inner edge wherein said outer edge and said inner edge are interconnected by a straight portion; and said tongues have a first portion comprising a circumferential arcuate shape having a radius of curvature less than or equal to the radius of curvature of said spherical lower surfaces of each of said recesses and a second portion comprising an elliptical shape which is an extension of said inner elliptical edge of each of said leaflets.

8. A prosthetic heart valve according to claim 7 wherein the closing movement of said leaflets is arrested when said tongues approach said upper surfaces of said recesses by the mutual contact of said inner edges of said leaflets, and by the contact of said outer edges of said leaflets with said inner surface of said base ring.

* * * * *